(12) United States Patent
Trieu et al.

(10) Patent No.: US 7,744,651 B2
(45) Date of Patent: *Jun. 29, 2010

(54) COMPOSITIONS AND METHODS FOR TREATING INTERVERTEBRAL DISCS WITH COLLAGEN-BASED MATERIALS

(75) Inventors: Hai H. Trieu, Cordova, TN (US); Michael C. Sherman, Memphis, TN (US)

(73) Assignee: Warsaw Orthopedic, Inc

(*) Notice: Subject to any disclaimer, the term of this patent is extended or adjusted under 35 U.S.C. 154(b) by 486 days.

This patent is subject to a terminal disclaimer.

(21) Appl. No.: 11/030,705

(22) Filed: Jan. 6, 2005

(65) Prior Publication Data

US 2005/0119754 A1 Jun. 2, 2005

Related U.S. Application Data

(63) Continuation-in-part of application No. 10/245,955, filed on Sep. 18, 2002, now abandoned.

(51) Int. Cl.
*A61F 2/44* (2006.01)

(52) U.S. Cl. .................. 623/17.16; 623/17.11

(58) Field of Classification Search .................. 623/1.1, 623/1.44, 1.47, 1.5–1.54, 23.72–23.76, 915, 623/917, 920, 921, 17.11, 23.58, 23.63, 17.16; 606/151

See application file for complete search history.

(56) References Cited

U.S. PATENT DOCUMENTS

| | | | |
|---|---|---|---|
| 3,551,560 A | 12/1970 | Thiele | |
| 3,855,638 A | 12/1974 | Pilliar | |
| 3,875,595 A | 4/1975 | Froning | |
| 4,060,081 A | 11/1977 | Yannas et al. | |
| 4,085,466 A | 4/1978 | Goodfellow et al. | |
| 4,185,813 A | 1/1980 | Spann | |
| 4,280,954 A | 7/1981 | Yannas et al. | |
| 4,344,193 A | 8/1982 | Kenny | |
| 4,349,921 A | 9/1982 | Kuntz | |
| 4,350,629 A | 9/1982 | Yannas et al. | |
| 4,378,224 A | 3/1983 | Nimni et al. | |
| 4,400,833 A | 8/1983 | Kurland | |

(Continued)

FOREIGN PATENT DOCUMENTS

EP 00305026 3/1988

(Continued)

OTHER PUBLICATIONS

Tay, B.K., et al., "Use of a Collagen-Hydroxyapatite Matrix in Spinal Fusion. A Rabbit Model," Spine, Vol. 23, No. 21, pp. 2276-2281, Nov. 1, 1998.
Burres, S., "Fascian," Facial Plast Surg, vol. 20, No. 2, pp. 149-152, May 2004.
Burres, S., "Midface Volume Replacement with a Transmaxiallary Implant," Aesthetic Plast Surg, vol. 29, No. 1, pp. 1-4, Jan.-Feb. 2005.
Burres, S., "Soft-tissue augmentation with fascian," Clin Plast Surg, vol. 28, No. 1, pp. 101-110, Jan. 2001. Abstract Only.
Burres, S., "Preserved Participate Fascia Lata for Injection: A New Alternative," vol. 25, No. 10, pp. 790-794, Oct 1999.
Burres, S., "Intralingual Injection of Particulate Fascia for Tongue Paralysis," Rhinological and Otological Society, Inc., The Laryngoscope, vol. 114, pp. 1204-1205, Jul. 2004.

(Continued)

*Primary Examiner*—Pedro Philogene

(57) ABSTRACT

A method of augmenting an intervertebral disc nucleus by injecting or otherwise adding to a disc nucleus a plurality of particles of natural, collagen-rich tissue. The mean particle size of the pieces of natural, collagen-rich tissue may be between 0.25 mm and 1.0 mm. The particles may be dehydrated before implantation, and rehydrated after implantation, or they may be implanted in a "wet" state—such as a slurry or gel. Radiocontrast materials may be included to enhance imaging of the injected material. Other additives may include analgesics, antibiotics, proteoglycans, growth factors, stem cells, and/or other cells effective to promote healing and/or proper disc function.

25 Claims, 12 Drawing Sheets

U.S. PATENT DOCUMENTS

| | | | |
|---|---|---|---|
| 4,418,691 A | 12/1983 | Yannas et al. | |
| 4,424,208 A | 1/1984 | Wallace et al. | |
| 4,448,718 A | 5/1984 | Yannas et al. | |
| 4,458,678 A | 7/1984 | Yannas et al. | |
| 4,505,266 A | 3/1985 | Yannas et al. | |
| 4,544,516 A | 10/1985 | Hughes et al. | |
| 4,578,079 A | 3/1986 | Ruoslahti et al. | |
| 4,582,640 A | 4/1986 | Smestad et al. | |
| 4,589,881 A | 5/1986 | Pierschbacher et al. | |
| 4,614,794 A | 9/1986 | Easton et al. | |
| 4,627,853 A | 12/1986 | Campbell et al. | |
| 4,642,117 A | 2/1987 | Nguyen et al. | |
| 4,642,120 A | 2/1987 | Nevo et al. | |
| 4,661,111 A | 4/1987 | Ruoslahti et al. | |
| 4,703,108 A | 10/1987 | Silver et al. | |
| 4,772,287 A | 9/1988 | Ray et al. | |
| 4,787,900 A | 11/1988 | Yannas | |
| 4,801,299 A | 1/1989 | Brendel et al. | |
| 4,803,075 A | 2/1989 | Wallace et al. | |
| 4,837,285 A | 6/1989 | Berg et al. | |
| 4,879,135 A | 11/1989 | Greco et al. | |
| 4,880,492 A | 11/1989 | Erdmann et al. | |
| 4,904,260 A | 2/1990 | Ray et al. | |
| 4,946,792 A | 8/1990 | O'Leary | |
| 4,976,733 A | 12/1990 | Giradot | |
| 5,007,934 A | 4/1991 | Stone | |
| 5,067,962 A | 11/1991 | Campbell et al. | |
| 5,106,949 A | 4/1992 | Kemp et al. | |
| 5,108,438 A | 4/1992 | Stone | |
| 5,137,514 A | 8/1992 | Ryan | |
| 5,192,326 A * | 3/1993 | Bao et al. | 623/17.12 |
| 5,229,497 A | 7/1993 | Boni | |
| 5,258,043 A | 11/1993 | Stone | |
| 5,397,352 A | 3/1995 | Burres | |
| 5,478,739 A | 12/1995 | Slivka et al. | |
| 5,507,810 A | 4/1996 | Prewett et al. | |
| 5,562,736 A * | 10/1996 | Ray et al. | 606/61 |
| 5,607,476 A | 3/1997 | Prewett et al. | |
| 5,713,959 A | 2/1998 | Bartlett et al. | |
| 5,733,337 A * | 3/1998 | Carr et al. | 435/325 |
| 5,788,625 A | 8/1998 | Plouhar et al. | |
| 5,858,747 A | 1/1999 | Schinstine et al. | |
| 5,916,870 A | 6/1999 | Lee et al. | |
| 5,922,028 A | 7/1999 | Plouhar et al. | |
| 5,935,849 A | 8/1999 | Schinstine et al. | |
| 5,948,428 A | 9/1999 | Lee et al. | |
| 5,964,807 A | 10/1999 | Gan et al. | |
| 5,976,186 A | 11/1999 | Bao et al. | |
| 5,980,504 A | 11/1999 | Sharkey et al. | |
| 5,994,325 A | 11/1999 | Roufa et al. | |
| 6,007,570 A | 12/1999 | Sharkey et al. | |
| 6,022,376 A | 2/2000 | Assell et al. | |
| 6,025,538 A | 2/2000 | Yaccarino, III | |
| 6,027,743 A | 2/2000 | Khouri et al. | |
| 6,046,379 A | 4/2000 | Stone et al. | |
| 6,073,051 A | 6/2000 | Sharkey et al. | |
| 6,077,989 A | 6/2000 | Kandel et al. | |
| 6,080,194 A | 6/2000 | Pachence et al. | |
| 6,080,579 A | 6/2000 | Hanley, Jr. et al. | |
| 6,095,149 A | 8/2000 | Sharkey et al. | |
| 6,099,514 A | 8/2000 | Sharkey et al. | |
| 6,122,549 A | 9/2000 | Sharkey et al. | |
| 6,123,731 A | 9/2000 | Boyce et al. | |
| 6,126,682 A | 10/2000 | Sharkey et al. | |
| 6,140,452 A | 10/2000 | Felt et al. | |
| 6,146,422 A | 11/2000 | Lawson | |
| 6,165,489 A | 12/2000 | Berg et al. | |
| 6,176,880 B1 | 1/2001 | Plouhar et al. | |
| 6,179,872 B1 | 1/2001 | Bell et al. | |
| 6,197,061 B1 | 3/2001 | Masuda et al. | |
| 6,224,630 B1 | 5/2001 | Bao et al. | |
| 6,240,926 B1 * | 6/2001 | Chin Gan et al. | 128/898 |
| 6,261,311 B1 | 7/2001 | Sharkey et al. | |
| 6,264,695 B1 | 7/2001 | Stoy | |
| 6,290,715 B1 | 9/2001 | Sharkey et al. | |
| 6,306,169 B1 | 10/2001 | Lee et al. | |
| 6,306,177 B1 | 10/2001 | Felt et al. | |
| 6,322,786 B1 | 11/2001 | Anderson | |
| 6,324,710 B1 | 12/2001 | Hernandez et al. | |
| 6,340,369 B1 | 1/2002 | Ferree et al | |
| 6,344,058 B1 | 2/2002 | Ferree | |
| 6,352,557 B1 | 3/2002 | Ferree | |
| 6,352,558 B1 | 3/2002 | Spector | |
| 6,402,784 B1 | 6/2002 | Wardlaw | |
| 6,419,702 B1 | 7/2002 | Ferree | |
| 6,425,919 B1 | 7/2002 | Lambrecht | |
| 6,428,576 B1 | 8/2002 | Haldimann | |
| 6,482,235 B1 * | 11/2002 | Lambrecht et al. | 623/17.16 |
| 6,592,625 B2 | 7/2003 | Cauthen | |
| 6,623,963 B1 | 9/2003 | Muller et al. | |
| 6,641,587 B2 | 11/2003 | Scribner et al. | |
| 6,648,918 B2 | 11/2003 | Ferree | |
| 6,662,805 B2 | 12/2003 | Frondoza et al. | |
| 6,699,294 B2 | 3/2004 | Urry | |
| 6,712,853 B2 | 3/2004 | Kuslich | |
| 6,716,251 B1 | 4/2004 | Asius et al. | |
| 6,723,335 B1 | 4/2004 | Moehlenbruck et al. | |
| 6,783,546 B2 | 8/2004 | Zucherman et al. | |
| 6,793,677 B2 | 9/2004 | Ferree | |
| 6,827,716 B2 | 12/2004 | Ryan et al. | |
| 6,929,640 B1 | 8/2005 | Underwood et al. | |
| 6,932,843 B2 | 8/2005 | Smith et al. | |
| 6,936,072 B2 | 8/2005 | Lambrecht et al. | |
| 6,939,329 B1 | 9/2005 | Verkaart | |
| 6,958,077 B2 | 10/2005 | Suddaby | |
| 6,969,404 B2 | 11/2005 | Ferree | |
| 6,980,862 B2 | 12/2005 | Fredricks et al. | |
| 7,060,103 B2 * | 6/2006 | Carr et al. | 623/23.72 |
| 2001/0006948 A1 | 7/2001 | Kang et al. | |
| 2001/0016195 A1 | 8/2001 | Tobinick | |
| 2001/0016772 A1 | 8/2001 | Lee et al. | |
| 2001/0020476 A1 | 9/2001 | Gan et al. | |
| 2001/0024823 A1 | 9/2001 | Vukicevic et al. | |
| 2001/0027199 A1 | 10/2001 | Olmarker et al. | |
| 2001/0051834 A1 | 12/2001 | Frondoza et al. | |
| 2001/0055594 A1 | 12/2001 | Olmarker et al. | |
| 2002/0029083 A1 | 3/2002 | Zucherman et al. | |
| 2002/0032155 A1 | 3/2002 | Ferree | |
| 2002/0038150 A1 | 3/2002 | Urry | |
| 2002/0049498 A1 | 4/2002 | Yuksel et al. | |
| 2002/0055143 A1 | 5/2002 | Bell et al. | |
| 2002/0115742 A1 | 8/2002 | Trieu et al. | |
| 2002/0116069 A1 | 8/2002 | Urry | |
| 2002/0120347 A1 | 8/2002 | Boyer, II et al. | |
| 2002/0133231 A1 | 9/2002 | Ferree | |
| 2002/0151979 A1 | 10/2002 | Lambrecht et al. | |
| 2002/0176893 A1 | 11/2002 | Wironen et al. | |
| 2003/0008817 A1 * | 1/2003 | Sander et al. | 514/12 |
| 2003/0104026 A1 | 6/2003 | Wironen et al. | |
| 2003/0130664 A1 | 7/2003 | Boucher et al. | |
| 2003/0158607 A1 | 8/2003 | Carr, Jr. et al. | |
| 2004/0010251 A1 | 1/2004 | Pitaru et al. | |
| 2004/0024081 A1 | 2/2004 | Trieu et al. | |
| 2004/0030392 A1 | 2/2004 | Lambrecht et al. | |
| 2004/0034429 A1 | 2/2004 | Lambrecht et al. | |
| 2004/0054414 A1 | 3/2004 | Trieu et al. | |
| 2004/0064023 A1 | 4/2004 | Ryan et al. | |
| 2004/0083001 A1 | 4/2004 | Kandel | |
| 2004/0083002 A1 | 4/2004 | Belef et al. | |
| 2004/0091540 A1 | 5/2004 | Desrosier et al. | |
| 2004/0092946 A1 | 5/2004 | Bagga et al. | |
| 2004/0101959 A1 | 5/2004 | Marko et al. | |
| 2004/0172132 A1 | 9/2004 | Ginn | |
| 2004/0220101 A1 | 11/2004 | Ferree | |

| | | | | | | |
|---|---|---|---|---|---|---|
| 2004/0220102 | A1 | 11/2004 | Ferree | EP | 15754548 A1 | 9/2005 |
| 2004/0228901 | A1 | 11/2004 | Trieu et al. | GB | 01515963 | 6/1978 |
| 2004/0229786 | A1 | 11/2004 | Attawia et al. | GB | 2407580 A | 5/2005 |
| 2004/0260397 | A1 | 12/2004 | Lambrecht et al. | JP | 2005103296 A | 4/2005 |
| 2005/0002909 | A1 | 1/2005 | Moehlenbruck et al. | JP | 2005118436 A | 5/2005 |
| 2005/0055094 | A1* | 3/2005 | Kuslich .......... 623/17.11 | JP | 2005152501 A | 5/2005 |
| 2005/0069571 | A1 | 3/2005 | Slivka et al. | WO | WO8910728 | 11/1989 |
| 2005/0070915 | A1 | 3/2005 | Mazzuca et al. | WO | 9210982 A1 | 7/1992 |
| 2005/0090915 | A1 | 4/2005 | Studer | WO | 9611642 A1 | 4/1996 |
| 2005/0100538 | A1 | 5/2005 | Mohamed et al. | WO | WO97/22371 | 6/1997 |
| 2005/0102030 | A1 | 5/2005 | Yuksel et al. | WO | 99/02108 A1 | 1/1999 |
| 2005/0113923 | A1 | 5/2005 | Acker et al. | WO | WO99/04720 | 2/1999 |
| 2005/0118228 | A1 | 6/2005 | Trieu | WO | WO99/43271 | 9/1999 |
| 2005/0119750 | A1 | 6/2005 | Studer | WO | 9961084 A1 | 12/1999 |
| 2005/0119754 | A1 | 6/2005 | Trieu | WO | 9962439 | 12/1999 |
| 2005/0125066 | A1 | 6/2005 | McAfee | WO | 0034556 A1 | 6/2000 |
| 2005/0131540 | A1 | 6/2005 | Trieu | WO | WO00/62832 | 10/2000 |
| 2005/0131541 | A1 | 6/2005 | Trieu | WO | WO00/75659 | 12/2000 |
| 2005/0143688 | A1 | 6/2005 | Lin et al. | WO | WO01/76654 | 10/2001 |
| 2005/0149007 | A1 | 7/2005 | Carl | WO | WO02/00142 | 1/2002 |
| 2005/0149046 | A1 | 7/2005 | Friedman et al. | WO | WO02/40070 | 5/2002 |
| 2005/0149197 | A1* | 7/2005 | Cauthen .......... 623/17.16 | WO | WO02/054978 | 7/2002 |
| 2005/0152986 | A1 | 7/2005 | Duneas et al. | WO | 03011155 A2 | 2/2003 |
| 2005/0154463 | A1 | 7/2005 | Trieu | WO | 03066120 A1 | 8/2003 |
| 2005/0159817 | A1 | 7/2005 | Ferree | WO | 03099230 A2 | 12/2003 |
| 2005/0177168 | A1 | 8/2005 | Brunnett et al. | WO | 2004002375 A1 | 1/2004 |
| 2005/0182414 | A1 | 8/2005 | Manzi et al. | WO | WO 2004026189 | 1/2004 |
| 2005/0182418 | A1 | 8/2005 | Boyd et al. | WO | 2004022155 A2 | 3/2004 |
| 2005/0186673 | A1 | 8/2005 | Geistlich et al. | WO | 2004026190 A2 | 4/2004 |
| 2005/0187543 | A1 | 8/2005 | Underwood et al. | WO | 2004028414 A1 | 4/2004 |
| 2005/0187556 | A1 | 8/2005 | Stack et al. | WO | 2004030548 A1 | 4/2004 |
| 2005/0191331 | A1 | 9/2005 | Hunter et al. | WO | 2004032808 A2 | 4/2004 |
| 2005/0196387 | A1 | 9/2005 | Seyedin et al. | WO | WO 2004093934 | 4/2004 |
| 2005/0197707 | A1 | 9/2005 | Trieu | WO | 2004041075 A2 | 5/2004 |
| 2005/0203206 | A1 | 9/2005 | Trieu | WO | WO 2004045667 | 6/2004 |
| 2005/0203527 | A1 | 9/2005 | Carrison et al. | WO | 2004060425 A2 | 7/2004 |
| 2005/0203537 | A1 | 9/2005 | Wiley et al. | WO | 2004064673 A2 | 8/2004 |
| 2005/0209595 | A1 | 9/2005 | Karmon | WO | 2004069296 A1 | 8/2004 |
| 2005/0209601 | A1 | 9/2005 | Bowman et al. | WO | 2004073532 A1 | 9/2004 |
| 2005/0209602 | A1 | 9/2005 | Bowman et al. | WO | 2004073563 A2 | 9/2004 |
| 2005/0222538 | A1 | 10/2005 | Embry et al. | WO | 2005000283 A2 | 1/2005 |
| 2005/0222684 | A1 | 10/2005 | Ferree | WO | 2005004755 A1 | 1/2005 |
| 2005/0234493 | A1 | 10/2005 | Carr et al. | WO | 2005032434 A1 | 4/2005 |
| 2005/0234498 | A1 | 10/2005 | Gronemeyer et al. | WO | 2005034781 A1 | 4/2005 |
| 2005/0234557 | A1 | 10/2005 | Lambrecht et al. | WO | 2005034800 A2 | 4/2005 |
| 2005/0240171 | A1 | 10/2005 | Forrest | WO | 2005041813 A2 | 5/2005 |
| 2005/0251259 | A1 | 11/2005 | Suddaby | WO | 2005049055 A1 | 6/2005 |
| 2005/0256580 | A1 | 11/2005 | Marissen | WO | 2005063316 A1 | 7/2005 |
| 2005/0261684 | A1 | 11/2005 | Shaolian et al. | WO | 2005070071 A2 | 8/2005 |
| 2005/0267580 | A1 | 12/2005 | Suddaby | WO | 2005070439 A1 | 8/2005 |
| 2005/0267583 | A1 | 12/2005 | Higham et al. | WO | 2005081870 A2 | 9/2005 |
| 2005/0273093 | A1 | 12/2005 | Patel et al. | WO | 2005092248 A1 | 10/2005 |
| 2005/0277996 | A1 | 12/2005 | Podhajsky | WO | 2005092249 A1 | 10/2005 |
| 2006/0019869 | A1 | 1/2006 | Thomas et al. | WO | 2005096978 A1 | 10/2005 |
| 2006/0044561 | A1 | 3/2006 | Nii | WO | 2005099392 A2 | 10/2005 |
| 2006/0196387 | A1 | 9/2006 | Hartley et al. | WO | 2005102433 A2 | 11/2005 |
| 2007/0026053 | A1 | 2/2007 | Pedrozo et al. | WO | 2005102440 A2 | 11/2005 |
| | | | | WO | 2005105168 A1 | 11/2005 |
| | | | | WO | 2005107827 A1 | 11/2005 |
| | | | | WO | 2005113032 A2 | 12/2005 |
| | | | | WO | 2005118015 A1 | 12/2005 |
| | | | | WO | 2006002417 A2 | 1/2006 |
| | | | | WO | 2006138098 A1 | 12/2006 |

FOREIGN PATENT DOCUMENTS

| | | |
|---|---|---|
| EP | 00277678 | 10/1988 |
| EP | 0747067 A2 | 12/1996 |
| EP | 1313412 A2 | 5/2003 |
| EP | 1407729 A1 | 4/2004 |
| EP | 1421957 A1 | 5/2004 |
| EP | 1328222 B1 | 3/2005 |
| EP | 1214026 B1 | 4/2005 |
| EP | 1198209 B1 | 5/2005 |
| EP | 1582166 A2 | 5/2005 |
| EP | 1051207 B1 | 8/2005 |
| EP | 1563808 A1 | 8/2005 |
| EP | 1563809 A2 | 8/2005 |

OTHER PUBLICATIONS

Shore, J. W., "Injectable Lyophilized Particulate Human Fascia Lata (Fascian) for Lip, Perioral, and Glabellar Enhancement," Ophthalmic Plastic and Reconstructive Surgery, vol. 16, No. 1, pp. 23-27, Jan. 2000.

* cited by examiner

COMPOSITIONS AND METHODS FOR TREATING INTERVERTEBRAL DISCS WITH COLLAGEN-BASED MATERIALS

REFERENCE TO RELATED APPLICATIONS

This application is a continuation-in-part and claims priority from U.S. patent application Ser. No. 10/245,955, filed Sep. 18, 2002 now abandoned. This application also contains subject matter disclosed in and claims priority from U.S. patent application Ser. No. 10/704,167, filed Nov. 7, 2003, which claims priority from U.S. application Ser. No. 60/426,613, filed Nov. 15, 2002. All of the above applications are incorporated herein by reference in their entirety.

FIELD OF THE INVENTION

The present invention relates generally to materials and methods for augmenting intervertebral discs and/or synovial joints, and more particularly to materials and methods for augmenting intervertebral discs and/or synovial joints with collagen-based materials.

BACKGROUND OF THE INVENTION

A healthy intervertebral disc facilitates motion between pairs of vertebrae while absorbing and distributing shocks. The disc is composed of two parts: a soft central core (the nucleus pulposus) that bears the majority of the load, and a tough outer ring (the annulus fibrosis) that holds and stabilizes the core material.

As the natural aging process progresses, the disc may dehydrate and degenerate, adversely affecting its ability to adequately cushion and support the vertebral bodies. This natural desiccation, which in its more advanced state is often referred to as "black disc" because of the disc's dehydrated appearance on Magnetic Resonance Imaging [MRI], can cause discomfort to the patient as the vertebrae to come closer together—compressing the spinal nerves and causing pain. Even in a less advanced degenerative state, such as when the disc annulus is substantially sound, surgical treatments for augmenting, repairing, or replacing the disc and/or the disc nucleus are indicated.

Techniques for addressing degenerative disc disease have heretofore relied primarily on disc replacement methods. In cases in which a dehydrated and/or degenerating disc was augmented before disc replacement was required, the augmentation materials have primarily been synthetic devices that expand, are inflated, or deploy expanding elements when implanted into the disc.

Synovial joints are the most common joints of the mammalian appendicular skeleton, representing highly evolved, movable joints. A typical synovial joint comprises two bone ends covered by layer of articular cartilage. The cartilage is smooth and resilient, and facilitates low-friction movement of the bones in the joint.

The bone ends and associated cartilage are surrounded by a joint capsule—a "sack" of membrane that produces synovial fluid. The capsule and fluid protect and support the cartilage and connective tissue, carrying nutrients to the articular cartilage and removing the metabolic wastes.

The articular cartilage is a thin (2-3 mm) layer of hyaline cartilage on the epiphysis of the bone. It lacks a perichondrium, and thus has a limited capacity for repair when damaged. Additionally, the natural aging process can cause the articular cartilage to degenerate somewhat, reducing its capacity to protect and cushion the bone ends.

Zygapophysial joints, better known as facet joints, are the mechanism by which each vertebra of the spine connects to the vertebra above and/or below it. Each joint comprises two facet bones—an inferior facet and a superior facet—with the inferior facet of one vertebra connecting to the superior facet of an adjacent vertebra. The joints facilitate movement of the vertebra relative to each other, and allow the spine to bend and twist.

As in all synovial joints, where the facets contact each other there is a lining of cartilage lubricated by a thin layer of synovial fluid. The cartilage and synovial fluid decrease friction at the joint, extending joint life and preventing inflammation and associated pain.

As the natural aging process progresses, the cartilage covering the joint may deteriorate and start to fray. The fraying process may cause pieces of cartilage to break free, and the previously smooth surfaces may become rough. The facet bones then begin to rub together, creating friction which leads to further deterioration of the joint. Moreover, the nerves associated with the joint become irritated and inflamed, causing severe pain and restricting movement of the spine.

Techniques for addressing degeneration of synovial joints in general, and facet joints in particular, joint have heretofore relied primarily on injections to block pain and reduce inflammation. This treatment is only temporary though, and rarely leads to any significant improvement of the underlying condition.

A need therefore exists for materials and methods effective for augmenting intervertebral discs and/or synovial joints with natural materials. The present invention addresses those needs.

SUMMARY OF THE INVENTION

Briefly describing one aspect of the present invention, there is provided a method of augmenting an intervertebral disc nucleus by injecting or otherwise adding to the disc nucleus a plurality of particles of natural, collagen-rich tissue. The mean particle size of the pieces of natural, collagen-rich tissue may be between 0.25 mm and 1.0 mm. The particles may be dehydrated before implantation, and rehydrated after implantation, or they may be implanted in a "wet" state—such as a slurry or gel. Radiocontrast materials may be included to enhance imaging of the injected material. Other additives may include analgesics, antibiotics, proteoglycans, growth factors, stem cells, and/or other cells effective to promote healing and/or proper disc function.

Objects and advantages of the claimed invention will be apparent from the following description.

BRIEF DESCRIPTION OF THE DRAWINGS

FIGS. 3A-1D show a procedure for injecting a collagen-based material into a facet joint, according to one preferred embodiment of the present invention.

FIGS. 4A-2F show a procedure for injecting a collagen-based material into a facet joint, according to another preferred embodiment of the present invention.

DESCRIPTION OF THE PREFERRED EMBODIMENTS

Figure 1A:
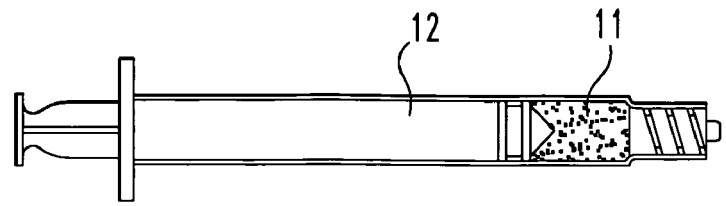
FIGS. 1A-1D show a procedure for injecting a collagen-based material into an intervertebral disc, according to one preferred embodiment of the present invention.

For the purposes of promoting an understanding of the principles of the invention, reference will now be made to certain preferred embodiments and specific language will be used to describe the same. It will nevertheless be understood that no limitation of the scope of the invention is thereby intended, such alterations and further modifications in the preferred embodiments being contemplated as would normally occur to one skilled in the art to which the invention relates.

As indicated above, one aspect of the present invention relates to materials and methods for using collagen-based material to treat a degenerating intervertebral disc or synovial joint. In the most preferred embodiments the collagen-based material is injected into the disc or the joint capsule. In some preferred embodiments the inventive method includes surgically adding to an intervertebral disc or a synovial joint a composition comprising particulate collagen-based material. In other embodiments the inventive method includes surgically adding to a disc or synovial joint a composition consisting essentially of particulate collagen-based material. The collagen-based material may be injected into a disc nucleus that is contained in a substantially sound annulus, or it may be injected into a disc nucleus that is contained in a damaged or defective annulus.

The collagen-based material may be derived from natural, collagen-rich tissue, such as intervertebral disc, fascia, ligament, tendon, demineralized bone matrix, etc. The material may be autogenic (autograft), allogenic (allograft), or xenogenic (xenograft), or it may be of human-recombinant origin. In alternative embodiments the collagen-based material may be a synthetic, collagen-based material. Examples of preferred collagen-rich tissues include disc annulus, fascia lata, planar fascia, anterior or posterior cruciate ligaments, patella tendon, hamstring tendons, quadriceps tendons, Achilles tendons, skins, and other connective tissues.

The collagen-based material may be provided in any form appropriate for introduction into a disc space or a synovial joint. For example, the material may be a solid, porous, woven, or non-woven material, and may be provided as particles, small pieces, gel, solution, suspension, paste, fibrous material, etc. The material may be used while it is still fresh and hydrated, or it may be used after having been processed, such as having been frozen and/or dehydrated.

In some embodiments the material is provided in a dehydrated state, and is "rehydrated" after injection in the joint. In other embodiments the material is implanted in a hydrated state. When the material is implanted in a hydrated state, it may be that way because it has never been dehydrated, or it may have been dehydrated and reconstituted. When reconstituted, the material may be reconstituted with saline or another aqueous medium, or it may be reconstituted with a non-aqueous medium such as ethylene glycol or another alcohol. Moreover, when provided in a "hydrated" state, the material may be provided as a gel, solution, suspension, dispersion, emulsion, paste, etc.

In the most preferred embodiments the material is a particulate and/or fibrous material suitable for injection through a hypodermic needle into a disc or synovial joint.

In the most preferred embodiments the collagen material is provided as particles ranging between 0.05 mm and 5 mm in size, or more preferably between 0.05 mm and 1.0 mm in size. When materials such as fascia lata or disc annulus particles are used the particles preferably range in size from 0.05 mm to 5 mm, or more preferably between 0.10 mm and 1.0 mm.

When materials such as demineralized bone matrix or gelatin are used the particles preferably range in size from 0.05 mm to 3 mm. When small plugs of material are used the plugs preferably range in size from 0.5 mm to 5 mm. In some embodiments larger sized pieces, such as pieces up to 20 mm in size, may be used. For the purposes of this description, the particle size is the largest dimension of a particle. Thus, a particle having a length of 1.0 mm, a width of 0.25 mm, and a height of 0.50 mm would have a "particle size" of 1.0 mm.

In some embodiments a natural, collagen-rich tissue having a mean particle size of between 0.25 mm and 1.0 mm is used. The mean particle size is the average particle size of the particles used in the treatment, i.e., when the particle size of each particle of collagen-rich material used in the treatment is considered, the mean particle size is the average of those sizes. In some alternative embodiments, a natural, collagen-rich tissue having a mean particle size of between 0.25 mm and 0.5 mm is used, while in other alternative embodiments a natural, collagen-rich tissue having a mean particle size of between 0.50 mm and 1.0 mm is used.

The materials may be processed or fabricated using more than one type of tissue. For example, mixtures of fascia lata and demineralized bone matrix may be preferred in appropriate cases, as may mixtures of DBM and annulus fibrosis material.

Cross-linking agents may be added to the formulation to promote cross-linking of the collagen material. For example, glutaraldehyde or other protein cross-linking agents may be included in the formulation. The cross-linking agents may promote covalent or non-covalent crosslinks between collagen molecules. Similarly, agents to inhibit protein denaturization may also be included. Crosslinking agents that would be appropriate for use in the claimed invention are known to persons skilled in the art, and may be selected without undue experimentation.

When the material is to be used as a slurry or gel, additives to promote slurry or gel formation may also be included. These additives may promote protein folding, water binding, protein-protein interactions, and water immobilization.

In addition, a radiographic contrast media, such as barium sulfate, or a radiocontrast dye, such as sodium diatrizoate (HYPAQUE®), may be included to aid the surgeon in tracking the movement and/or location of the injected material. Radiocontrast materials appropriate for use in discography are known to persons skilled in the art, and may be selected for use in the present invention without undue experimentation.

Finally, other additives to provide benefits to the injected collagen-based material may also be included. For example, pharmacological agents such as growth factors that may advantageously repair the endplates and/or the annulus fibrosis may be included. The growth factor may include a bone morphogenetic protein, transforming growth factor-$\beta$ (TGF-$\beta$), insulin-like growth factor, platelet-derived growth factor, fibroblast growth factor or other similar growth factor or combination thereof having the ability to repair the endplates and/or the annulus fibrosis of an intervertebral disc.

The growth factors are typically included in the implants in therapeutically effective amounts. For example, the growth factors may be included in the implants in amounts effective in repairing an intervertebral disc, including repairing the endplates and the annulus fibrosis. Such amounts will depend on the specific case, and may thus be determined by the skilled artisan, but such amounts may typically include less than about 1% by weight of the growth factor. The growth factors may be purchased commercially or may be produced by methods known to the art. For example, the growth factors may be produced by recombinant DNA technology, and may preferably be derived from humans. As an example, recombinant human bone morphogenetic proteins (rhBMPs), including rhBMP 2-14, and especially rhBMP-2, rhBMP-7, rhBMP-12, rhBMP-13, and heterodimers thereof may be used. However, any bone morphogenetic protein is contemplated including bone morphogenetic proteins designated as BMP-1 through BMP-18.

BMPs are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All bone morphogenic proteins are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In other forms of the invention, the pharmacological agent may be one used for treating various spinal conditions, including degenerative disc disease, spinal arthritis, spinal infection, spinal tumor and osteoporosis. Such agents include antibiotics, analgesics, anti-inflammatory drugs, including steroids, and combinations thereof. Other such agents are well known to the skilled artisan. These agents are also used in therapeutically effective amounts. Such amounts may be determined by the skilled artisan depending on the specific case.

The pharmacological agents are preferably dispersed within the collagen-based material for in vivo release. The pharmacological agents may be dispersed in the material by soaking the material in an appropriate solution containing the agent, or by other appropriate methods known to the skilled artisan. In other forms of the invention, the pharmacological agents may be chemically or otherwise associated with the material. For example, the agents may be included in the fluid phase in which the collagen-based material is suspended or otherwise dispersed.

Polysaccharides such as proteoglycans and/or hyaluronic acid may also be included to attract and/or bind water to keep the disc or synovial joint hydrated. Additionally, growth factors and/or other cells (e.g., intervertebral disc cells, stem cells, etc.) to promote healing, repair, regeneration and/or restoration of the joint, and/or to facilitate proper joint function, may also be included. Additives appropriate for use in the claimed invention are known to persons skilled in the art, and may be selected without undue experimentation.

In some embodiments the collagen material is dehydrated before injection into the disc or joint, where it is rehydrated by absorbing fluid from the surrounding area. In other embodiments the collagen material is provided as a gel, slurry, or other hydrated formulation before implantation.

The collagen-based material is "surgically added" to the intervertebral disc or the synovial joint. That is, the material is added by the intervention of medical personnel, as distinguished from being "added" by the body's natural growth or regeneration processes. The surgical procedure preferably includes injection through a hypodermic needle, although other surgical methods of introducing the collagen-based material into the disc or joint may be used. For example, the material may be introduced into a disc or synovial joint by extrusion with an extruder through a dilated opening, infusion through a catheter, insertion through an opening created by trauma or surgical incision, or by other means of invasive or minimally invasive deposition of the materials into the disc or joint space.

When the collagen-based material is combined with another biologically active substance, the two materials may be added to the disc nucleus together or separately. For example, the two materials may be added simultaneously by mixing the materials together and then adding them with a single barrel syringe, or by leaving the materials unmixed in a double barrel syringe and using a mixing tip to simultaneously inject the two materials. Alternatively, the two materials may be added sequentially using a hypodermic needle or other means of implanting the material.

Figure 1B:
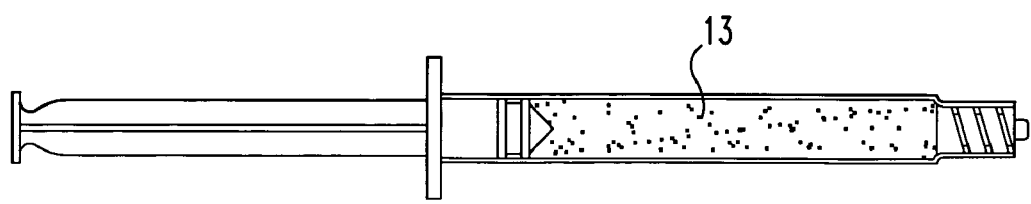
Figure 1C:
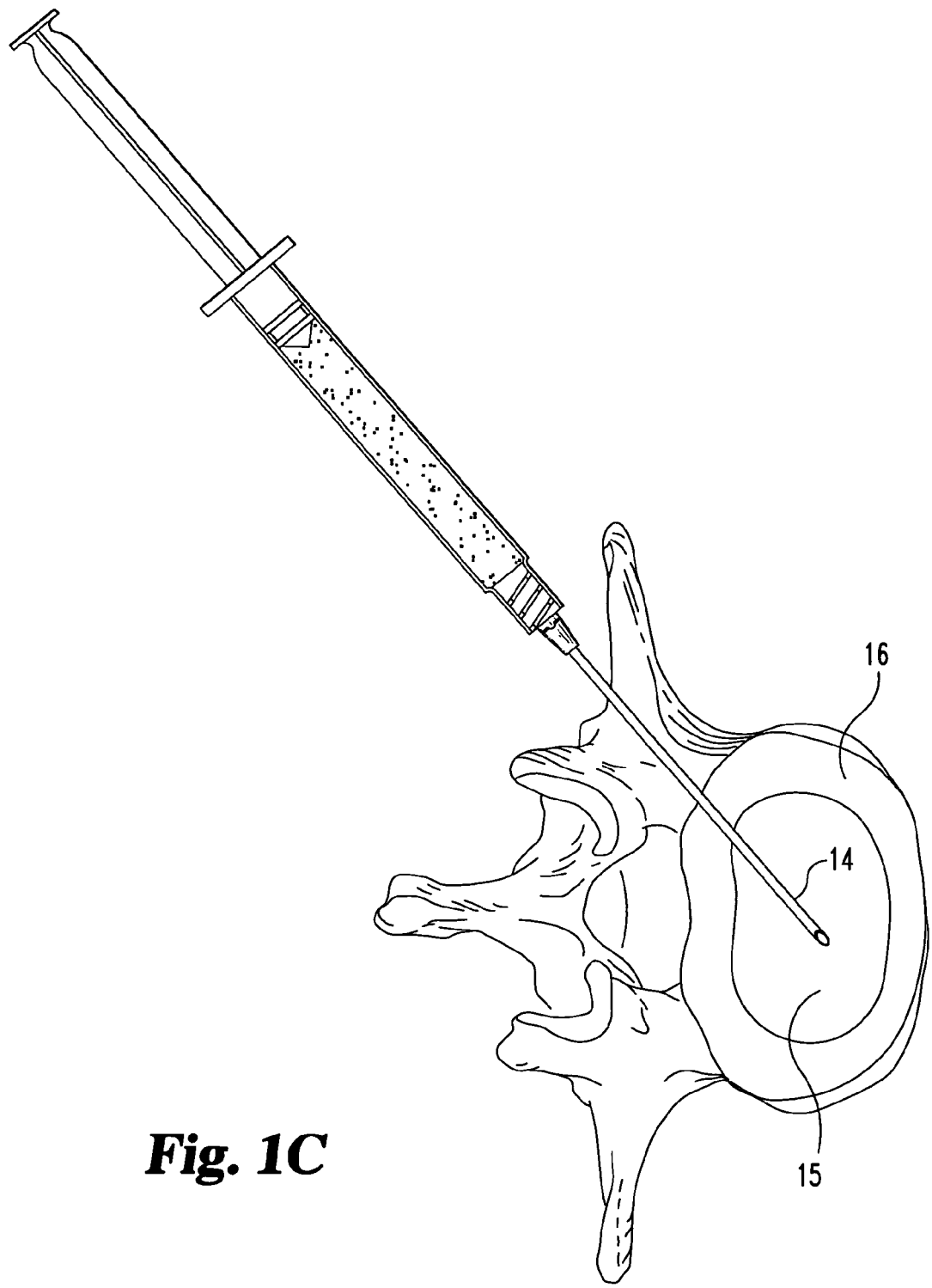
Figure 1D:
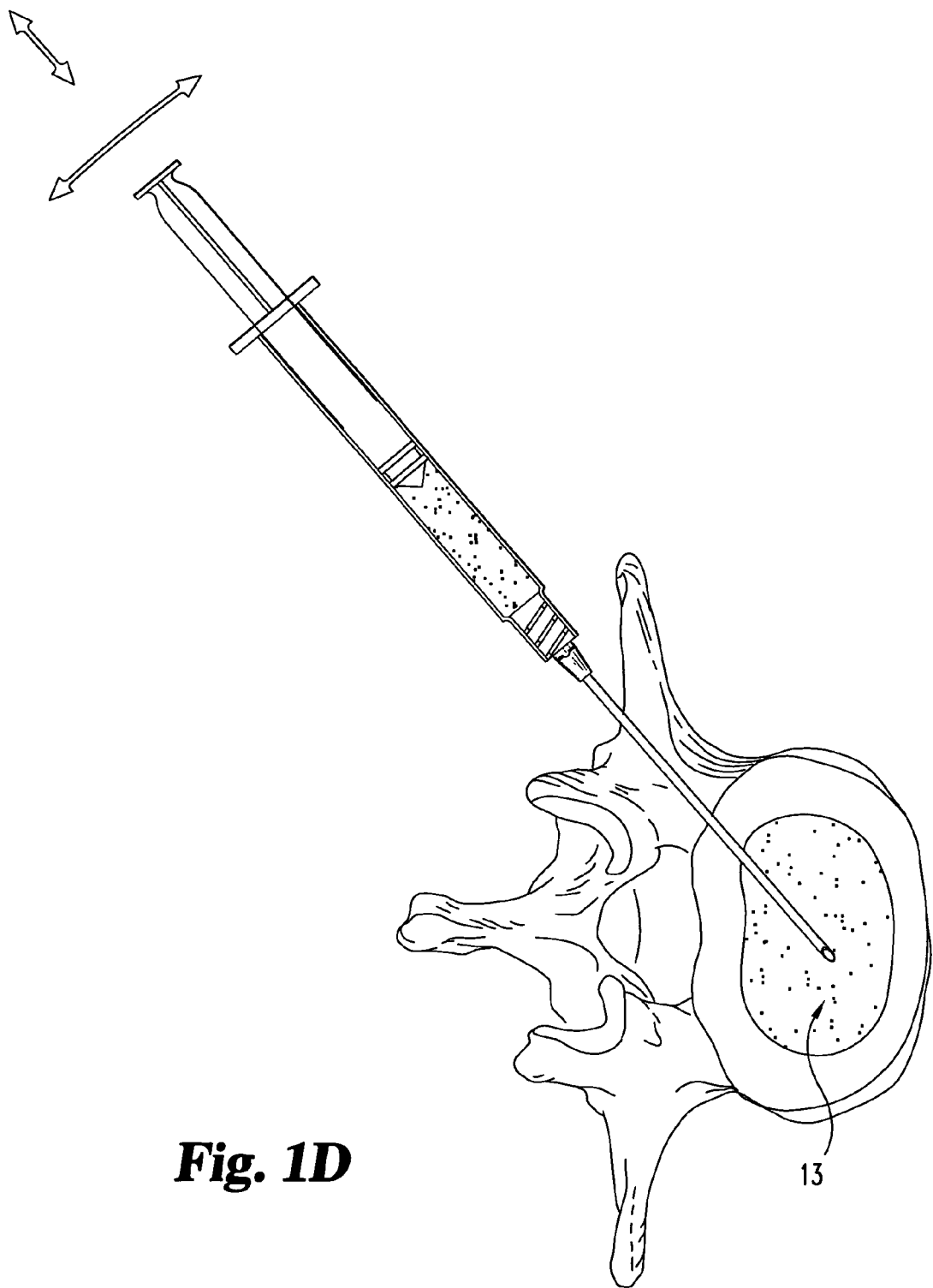

Referring now to the drawings, FIGS. 1A-1D show one method of injecting a collagen-based material into a disc. In FIG. 1A, dehydrated particulate fascia lata or annulus fibrosis material 11 is provided in a syringe 12 (in a sterile package). The material is rehydrated and/or dispersed in a suspension medium as shown in FIG. 1B, to provide a wet dispersion 13 of collagen-based material. A hypodermic needle 14 is attached to syringe 12, and the syringe is inserted into a nucleus pulposus 15 contained within a disc annulus 16 (FIG. 1C). The needle/syringe may be moved around within the disc space, sweeping from side to side and back and forth, to ensure uniform distribution of the collagen-based material 13 within the disc space, as shown in FIG. 1D. It is preferred, however, that the tip of the needle be maintained near the center of the disc to ensure deposition of the material within the nuclear disc space, and to minimize potential leakage.

Figure 2A:
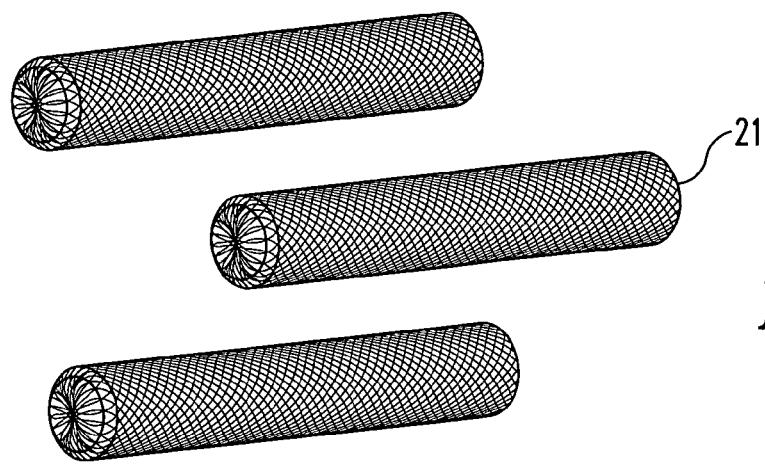
FIGS. 2A-2F show a procedure for injecting a collagen-based material into an intervertebral disc, according to another preferred embodiment of the present invention.
Figure 2B:
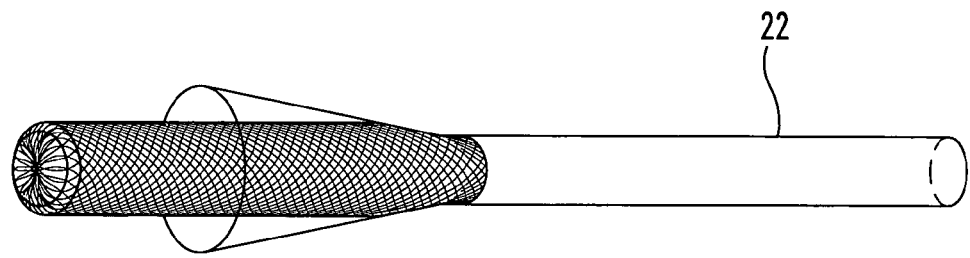
Figure 2C:

Alternatively, small collagen plugs 21 may be inserted into the disc space as shown in FIGS. 2A-2F. The collagen plugs 21 may be compressed before or by insertion into a small diameter tube 22, and are provided in a delivery cannula 23 (FIGS. 2A-2C). The delivery cannula 23 is attached to a dilator 24.

Figure 2D:
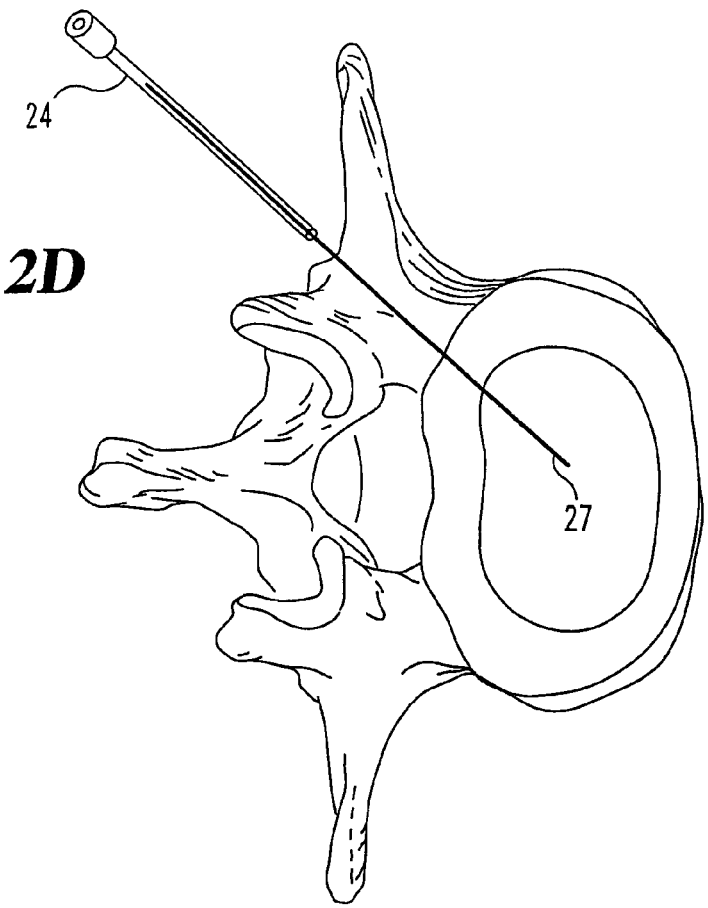
Figure 2E:
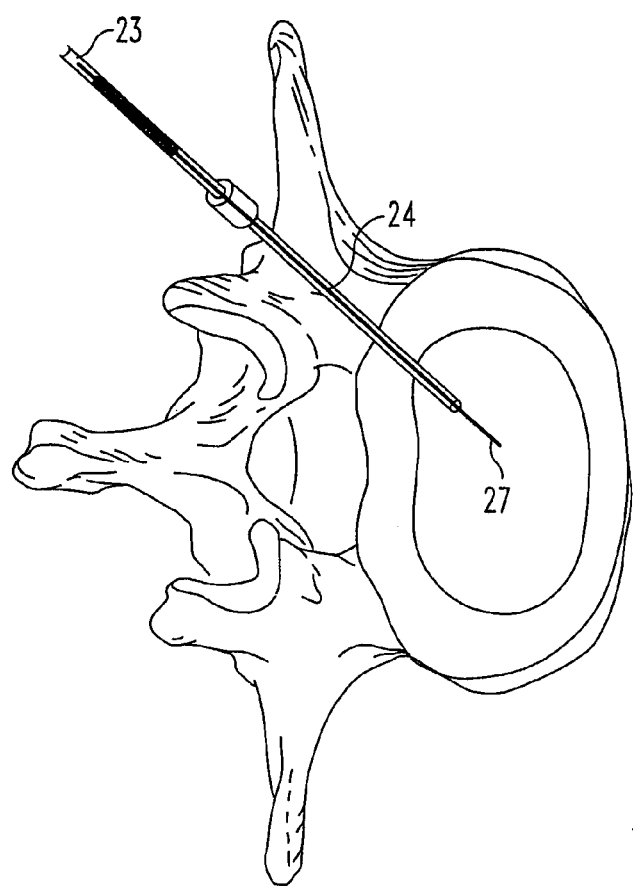
Figure 2F:
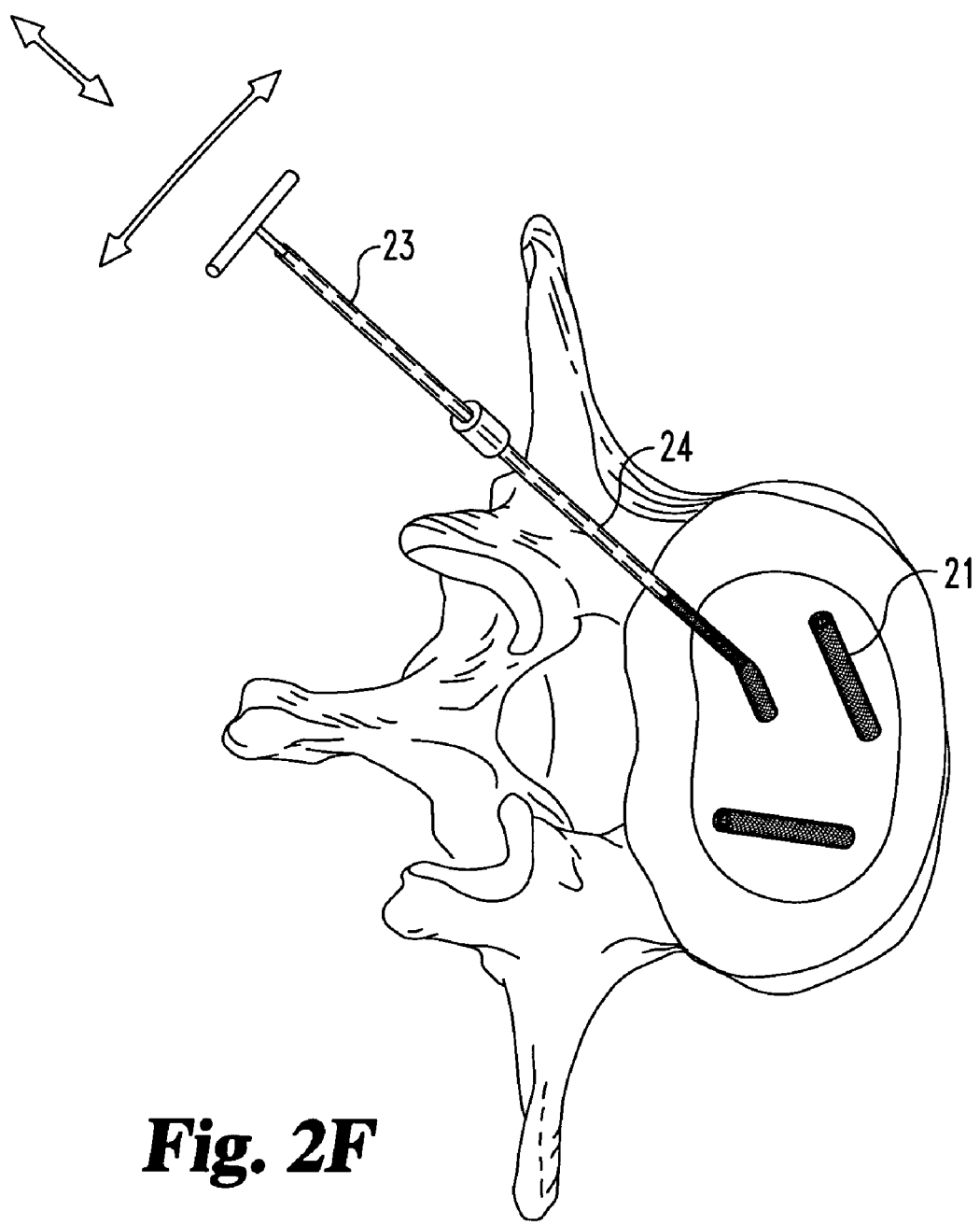
Figure 3A:
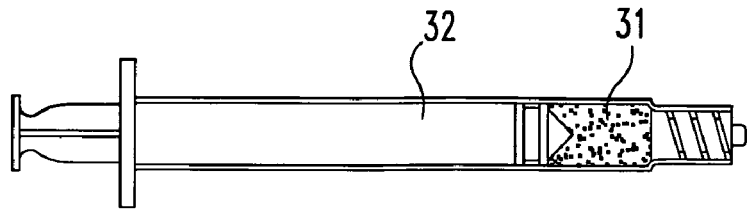
Figure 3B:
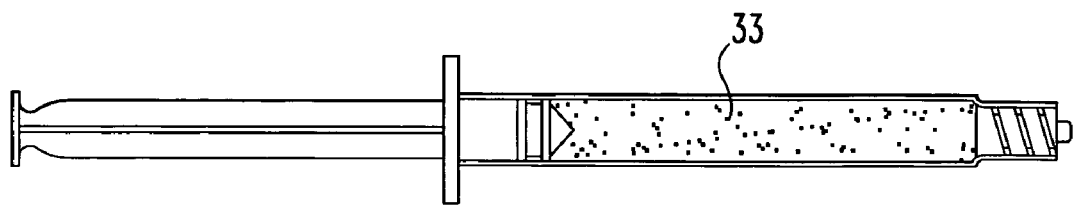
Figure 3C:
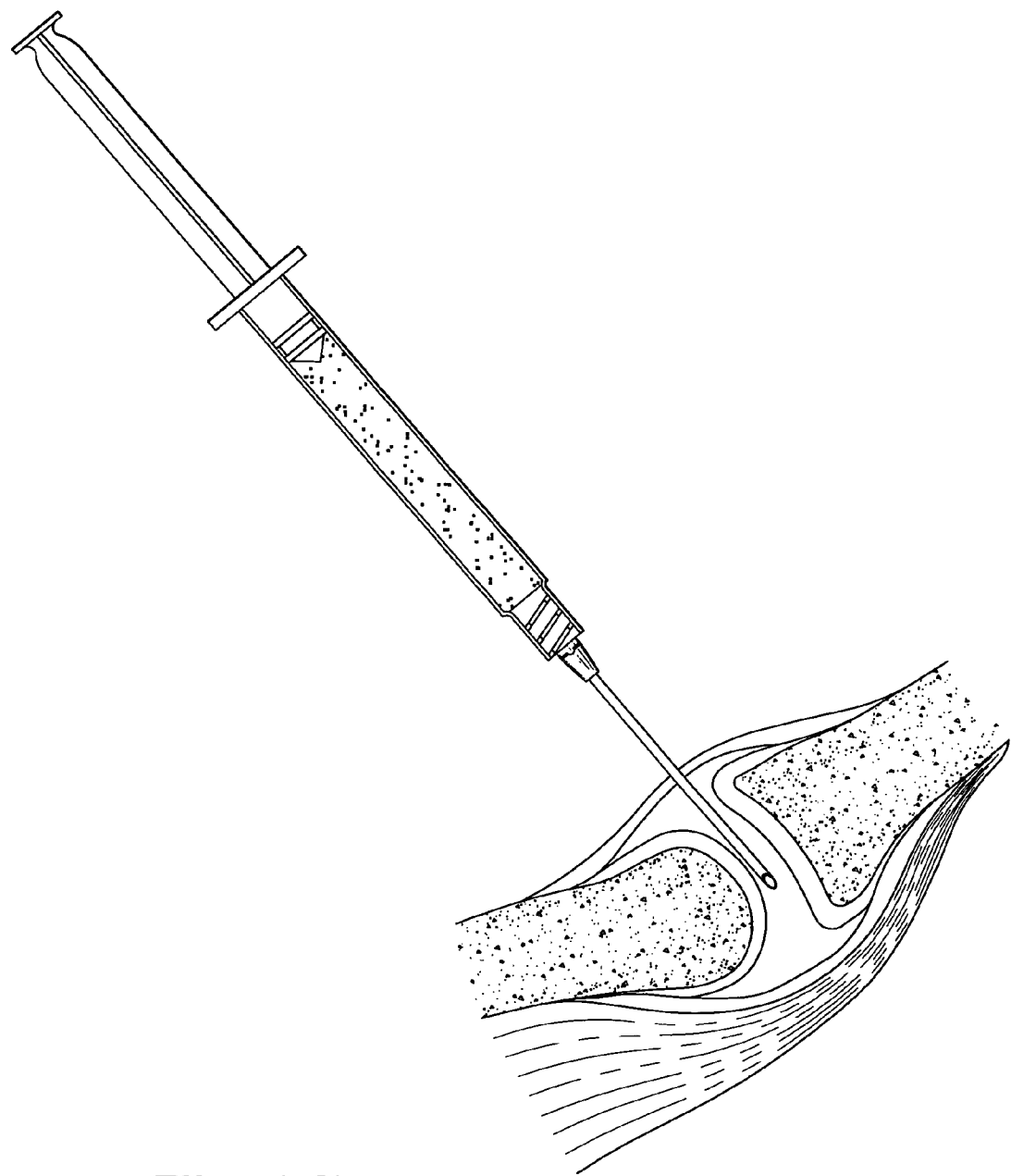
Figure 3D:
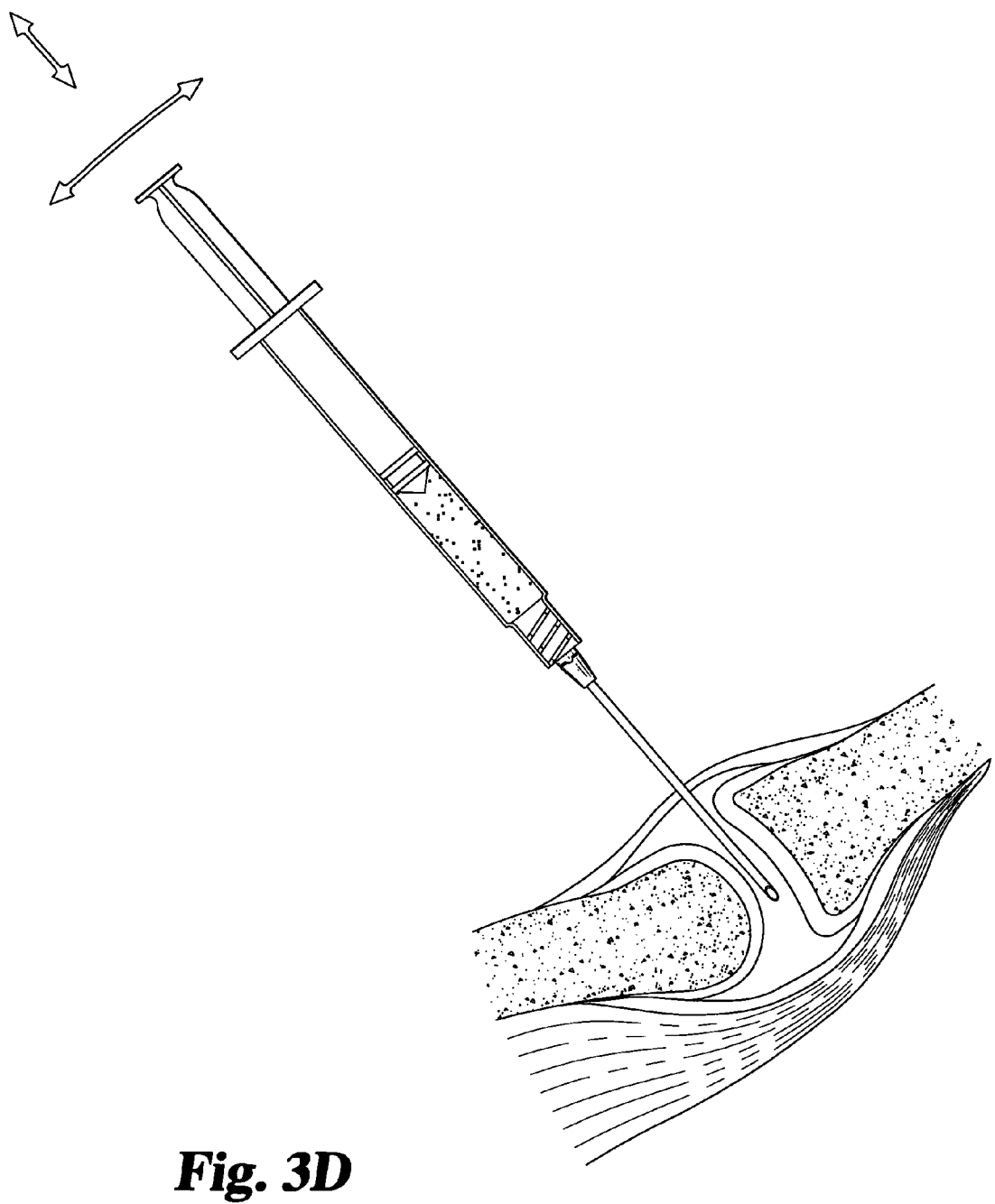
Figure 4A:
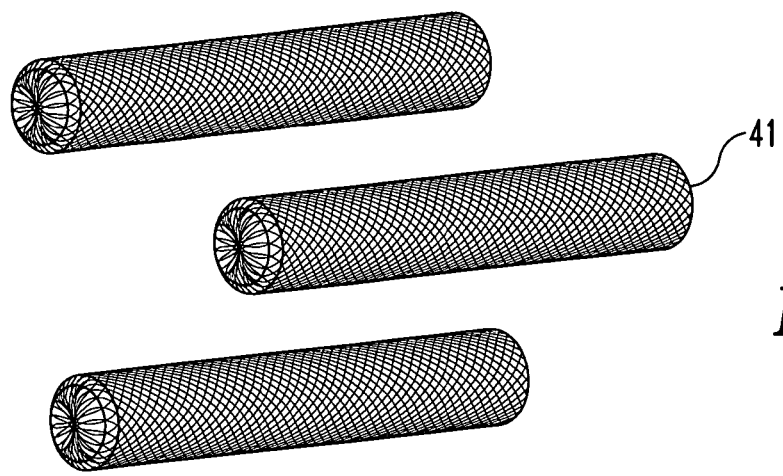
Figure 4B:
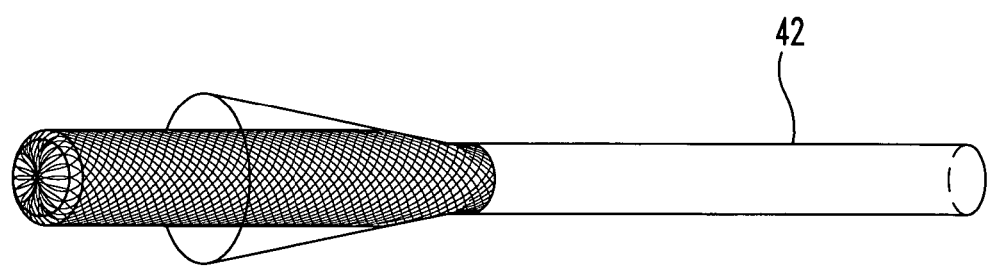
Figure 4C:
Figure 4D:
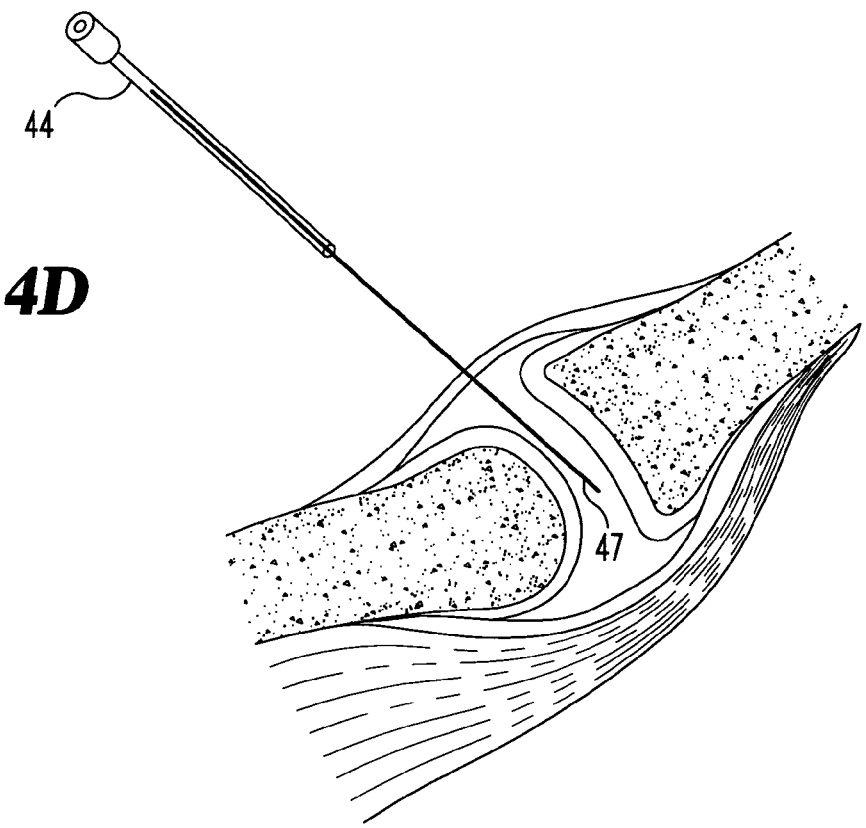
Figure 4E:
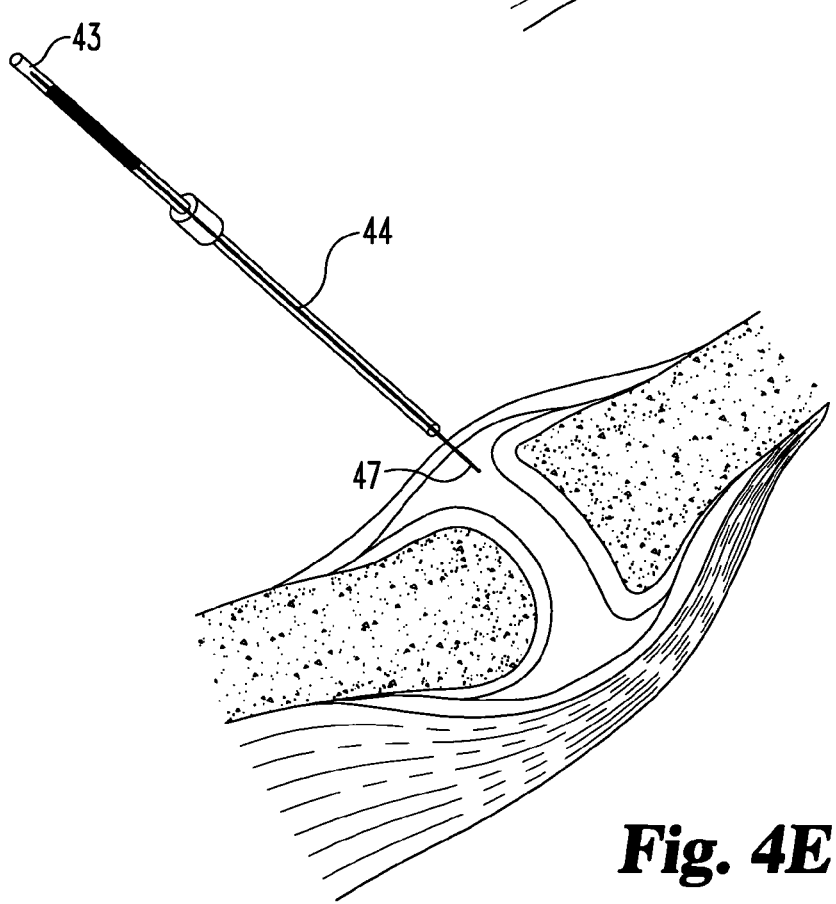
Figure 4F:
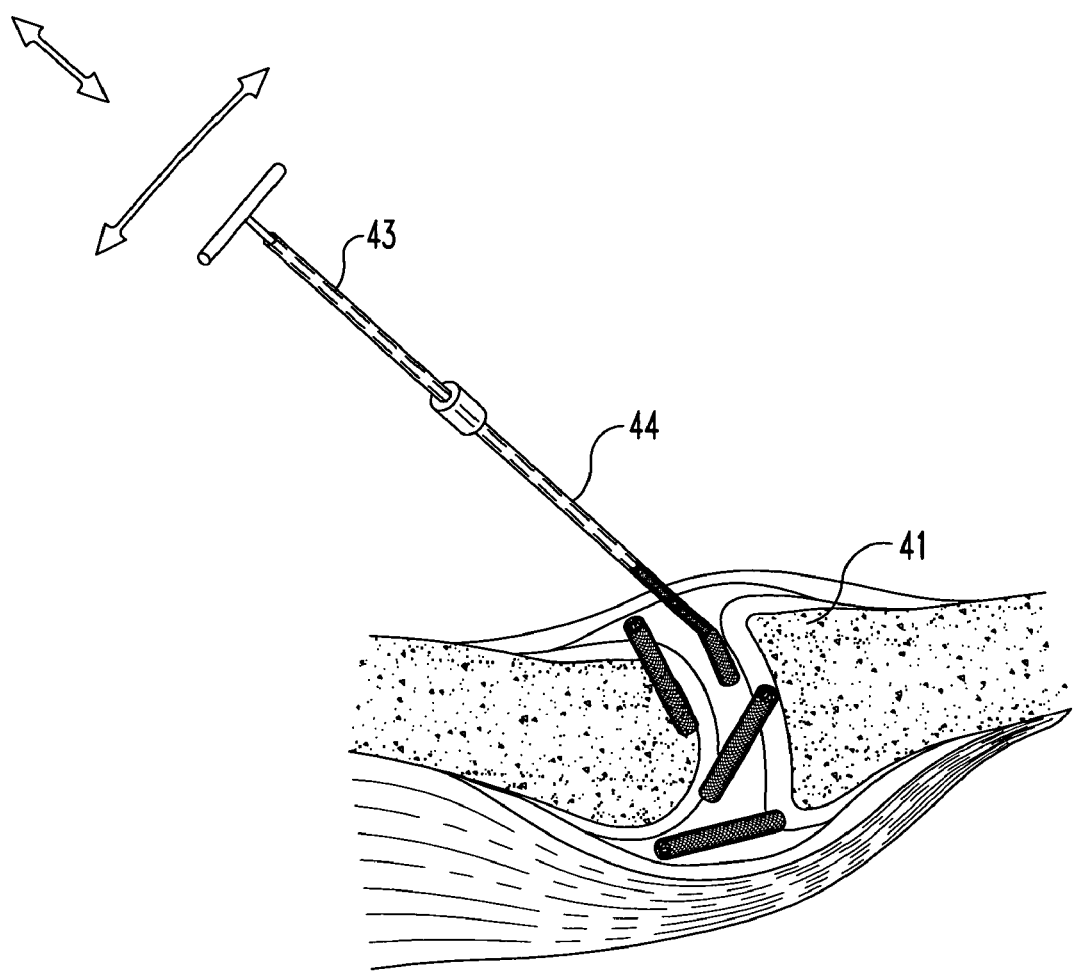

The compressed plugs are inserted into a disc nucleus 25 having a substantially intact annulus 26 by penetrating the annulus with a guide needle 27 (FIG. 2D). Dilator 24, preferably with delivery cannula 23 already attached, is inserted through the annulus over guide needle 27 (FIG. 2E). The collagen plugs 21 are then ready for injection (or extrusion) into the disc space.

The collagen plugs are deposited into the disc space. As with the wet particulate/fibrous material, the cannula may be moved up and back, and/or side to side, to ensure even distribution of the plugs (FIG. 2F) a plunger 28 may be used to push the plugs from the cannula.

The plugs expand upon exiting the dilator, and may further expand as they rehydrate in the disc space.

Benefits and advantages arising from use of the materials and methods of the present invention may include:

(1) the invention provides lubrication and/or cushioning to degenerated synovial joints, improving or restoring proper joint function;

(2) the rehydration provided by the invention is expected to slow the degenerative process;

(3) the invention relieves pain due to improved lubrication of the joint;

(4) the procedure is percutaneous or a minimally invasive outpatient procedure;

(5) the risks are minimal, as similar techniques and materials are used in cosmetic procedures;

(6) the materials are biocompatible since natural or human-recombinant collagen-based materials are used;

As previously indicated, in other preferred embodiments the materials and methods of the present invention may be used to treat synovial joints in the spine, particularly facet joints. In other preferred embodiments hip, knee, ankle, finger, toe, elbow, shoulder, wrist, sacroiliac, temporomandibular, carpometacarpal, etc., joints may all be treated by injecting a collagen-source material into the joint space to supplement/augment the cartilage that lubricates the joint. Advantages commensurate with those identified above may be obtained by the use of such alternative embodiments.

Reference will now be made to specific examples using the processes described above. It is to be understood that the examples are provided to more completely describe preferred embodiments, and that no limitation to the scope of the invention is intended thereby.

EXAMPLE 1A

Hydrated Particulate Fascia Lata

A suspension of particulate or fibrous (autologous or allogenic) fascia lata is prepared in a biocompatible medium such as saline or ethylene glycol. The particle size ranges from 0.1 mm to 5 mm, with most particles being between 0.25 and 2 mm.

The suspension is injected directly into the nuclear disc space through an intact annulus using a hypodermic needle, and is contained within the disc space following injection. The medium subsequently diffuses out of the disc space and leaves the fascia lata material behind.

Inspection of the disc reveals that an appropriate level of augmentation may be obtained with a single injection of material. Alternatively, several smaller doses/injections may be used to achieve comparable results.

EXAMPLE 1B

Hydrated Particulate Fascia Lata with Crosslinking Agent

A suspension of particulate or fibrous (autologous or allogenic) fascia lata is prepared in a biocompatible medium such as saline or ethylene glycol. The particle size ranges from 0.1 mm to 5 mm, with most particles being between 0.25 mm and 2 mm. A glutaraldehyde crosslinking agent is added to promote collagen crosslinking.

The suspension is injected directly into the nuclear disc space through an intact annulus using a hypodermic needle, and is contained within the disc space following injection. The medium subsequently diffuses out of the disc space and leaves the fascia lata material behind.

Inspection of the disc reveals that an appropriate level of augmentation may be obtained through either a single injection of material, or by multiple injections.

EXAMPLE 1C

Dehydrated Particulate Fascia Lata

Dehydrated fascia lata material is provided in particulate form. Particle sizes range between 0.05 mm and 3 mm, with most particles being between 0.10 mm and 1 mm. The dehydrated material is loaded in a specially designed syringe for delivery of solid materials.

The material is extruded into the nuclear disc space of the treated disc through a small dilated annular opening. The material remains inside the disc space after the needle is removed. It subsequently absorbs moisture or body fluids and swells up in vivo.

Inspection of the disc reveals that an appropriate level of augmentation may be obtained through either a single injection of material, or by multiple injections.

EXAMPLE 2A

Hydrated Particulate Disc Annulus Material

A suspension of particulate or fibrous allogenic annulus fibrosis is prepared in a biocompatible medium such as saline or ethylene glycol. The particle size ranges from 0.1 mm to 5 mm, with most particles being between 0.25 and 2 mm.

The suspension is injected directly into the nuclear disc space through an intact annulus using a hypodermic needle. The suspension is contained within the disc space following injection. The medium subsequently diffuses out of the disc space and leaves the annulus fibrosis material behind.

Inspection of the disc reveals that an appropriate level of augmentation may be obtained through either a single injection of material, or by multiple injections.

EXAMPLE 2B

Hydrated Particulate Disc Annulus Material with Crosslinking Agent

A suspension of particulate or fibrous allogenic annulus fibrosis is prepared in a biocompatible medium such as saline or ethylene glycol. The particle size ranges from 0.1 mm to 5 mm, with most particles being between 0.25 and 2 mm. A glutaraldehyde crosslinking agent is added to promote collagen crosslinking.

The suspension is injected directly into the nuclear disc space through an intact annulus using a hypodermic needle. The suspension is contained within the disc space following injection. The medium subsequently diffuses out of the disc space and leaves the annulus fibrosis material behind.

Inspection of the disc reveals that an appropriate level of augmentation may be obtained through either a single injection of material, or by multiple injections.

EXAMPLES 3A-3C

Dehydrated Annulus Fibrosis

Dehydrated annulus fibrosis is provided in granule, particulate and powder form, for example 3A-3C respectively. Particle sizes range between 0.05 mm and 3 mm, with most particles being between 0.10 mm and 1 mm. The dehydrated material is loaded in a specially designed syringe for delivery of solid materials.

The material is extruded into the nuclear disc space of the treated disc through a small dilated annular opening. The material remains inside the disc space after the needle is removed. It subsequently absorbs moisture or body fluids and swells up in vivo.

Inspection of the disc reveals that an appropriate level of augmentation may be obtained through either a single injection of material, or by multiple injections.

EXAMPLES 4A-4B

Demineralized Bone Matrix (DBM) Gel

Demineralized bone matrix (DBM) gel is provided with and without glutaraldehyde as a cross-linker additive (examples 4A and 4B, respectively). In both cases the material is warmed up to an appropriate temperature for melting or thinning out the gel, and is injected directly into the nuclear disc space through an intact annulus using a hypodermic needle. The DBM gel becomes solidified in the disc space after injection.

Inspection of the disc reveals that an appropriate level of augmentation may be obtained through either a single injection of material, or by multiple injections.

EXAMPLES 4C

Dehydrated Demineralized Bone Matrix (DBM)

Dehydrated DBM is provided in granule, particulate and powder form. Particle sizes range between 0.05 mm and 3 mm, with most particles being between 0.10 mm and 1 mm. The dehydrated material is loaded in a specially designed syringe for delivery of solid materials.

The material is extruded into the nuclear disc space of the treated disc through a small dilated annular opening. The material remains inside the disc space after the needle is removed. It subsequently absorbs moisture or body fluids and swells up in vivo.

Inspection of the disc reveals that an appropriate level of augmentation may be obtained through either a single injection of material, or by multiple injections.

EXAMPLE 5A-5D

Mixtures of Annulus Fibrosis and Demineralized Bone Matrix

Mixtures of particulate and fibrous allogenic annulus fibrosis and demineralized bone matrix (DBM) gel, with and without additives and/or cross-linkers, are provided. The materials are warmed up to an appropriate temperature for melting or thinning out the gel mixture, and are injected directly into the nuclear disc space through an intact annulus using a hypodermic needle. The gel mixture becomes solidified in the disc space after injection.

Inspection of the disc reveals that an appropriate level of augmentation may be obtained through either a single injection of material, or by multiple injections.

EXAMPLE 6

Elongated cylindrical plugs (0.5 mm to 5 mm in diameter, preferably 1 mm to 2 mm) of solid, porous, or fibrous collagen are provided in a dehydrated state. The plugs are compressed in the radial direction and are inserted into delivery cannula for delivery into disc space.

A guide wire or needle is used to penetrate the disc space through an intact annulus. A dilator is subsequently inserted into the disc space over the guide wire/needle, and the guide wire/needle is removed. The delivery cannula containing a collagen plug is attached to the dilator prior to extrusion of the plug into the disc space. As the plugs absorb moisture after entering the disc space, they become more compliant, flexible and expanded.

The level of disc augmentation achieved depends on the number of plugs inserted, and/or on the total plug volume deposited in the disc space.

EXAMPLE 7

Cylindrical plugs or rolls (2 mm-20 mm in diameter, preferably 10-15 mm) of solid, porous, or fibrous collagen are provided in a dehydrated state. The dehydrated plugs are typically more rigid than those in hydrated state, and thus, can be easily inserted into the disc space through an annular opening created by trauma or surgical incision.

Nucleotomy is necessary before the plug can be inserted. As the plugs absorb moisture after entering the disc space, they become more compliant, flexible and expanded.

The level of disc augmentation/replacement achieved depends on the size and number of plugs inserted into the disc space.

EXAMPLE 8

Particulate fascia used for cosmetic procedure (FASCIAN®) was modified to include a radiocontrast media. A small quantity of barium sulfate powder was blended with 80 mg of >0.5 mm Gastrocemius Fascia for visualization under fluoroscopic imaging. About 1-1.5 cc of water was added to the blend in the syringe for hydration.

After hydration for 5-10 minutes, the material (Fascian/Barium Sulfate/Water or F.B.W.) was injected into the nuclear disc space of a harvested porcine intervertebral disc. X-ray images of the disc were obtained before and after injection.

A small increase in disc height was noticed after injection. Also, manual compression indicated that the disc was stiffer after injection. The injected disc was also tested under compression up to 5000N. There was no gross leakage observed during the compression test. Only a slight oozing of a small amount of injected material was observed at the injection site, but it stopped quickly.

The disc was cut in the horizontal plane to confirm the location of the injected material. F.B.W. was found contained within the disc annulus and mixed in with nucleus pulposus.

EXAMPLE 9

Particulate fascia used for cosmetic procedures (FASCIAN®) was modified before experimentation to include a radiocontrast material. A small quantity of radio-contrast dye or barium sulfate powder was blended with about 200 mg of 0.25-1.0 mm Gastrocemius Fascia for visualization under fluoroscopic imaging. About 1.5-3 cc of saline was added to the blend in the syringe for hydration.

After hydration for about 30 minutes, the material (Fascian/Dye or Barium Sulfate/Water) was injected into the nuclear disc space of cadaveric intervertebral discs (L2-3 and L3-4). X-ray images of the discs were obtained before and after injection. A small increase in disc height was noticed radiographically after injection. There was no gross leakage observed at the injection site. In the case of L3-4 injection, the needle tip was maintained approximately at the center of the disc, which resulted in material deposition mainly within the nucleus pulposus.

EXAMPLE 10

Particulate fascia (FASCIAN®) having particle sizes of 0.25 mm and 0.5 mm was purchased from Fascia BioSystems. Collagen solutions were prepared, with each solution consisting of approximately 80 mg of particulate fascia, 0.75 ml of saline, and 0.25 ml HYPAQUE® radiocontrast solution.

Thoracic and lumbar discs in two pigs were subjected to stabbing injury. The injured discs were then injected with 1-2 ml of collagen solution at 4 weeks after injury. The injections were performed using a 3 ml syringe, a 20 gauge hypodermic needle and a graft placement device. Confirming X-ray was taken using C-arm fluoroscopy.

The injured discs appeared to have somewhat reduced heights at four weeks after injury. Of approximately 12 injected discs, only one leakage was observed. The amount of leakage was estimated to be less than 20% of the total volume injected. The low incidence of leakage indicates that the annulus is capable of self-sealing when a small gauge needle is used for injection.

The disc height increased upon collagen injection depending on the injected volume. In particular, an approximately 46% increase in disc height was achieved with 2 ml injection. In some cases the disc height gain was reduced after injection as radio-contrast dye and water molecules diffused out of the disc under intra-discal pressure.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of augmenting an intervertebral disc nucleus, said method comprising surgically adding to an intervertebral disc nucleus contained within a disc annulus an injectable material including:
   a) a plurality of particles of natural tissue selected from the group consisting of intervertebral disc, fascia, ligament, tendon, skin, and other connective tissue, wherein said plurality of particles of natural, collagen-rich tissue has a mean particle size of between 0.05 mm and 5.0 mm; and
   b) a biologically active substance effective to promote healing, repair, regeneration and/or restoration of the disc, and/or to facilitate proper disc function.

2. The method of claim 1 wherein said biologically active substance is a growth factor.

3. The method of claim 2 wherein said growth factor comprises one or more members selected from, the group consisting of bone morphogenetic protein, transforming growth factor-β (TGF-β), insulin-like growth factor, platelet-derived growth factor, fibroblast growth factor, or other growth factors having the ability to repair the endplates and/or the annulus fibrosis of an intervertebral disc.

4. The method of claim 1 wherein said biologically active substance comprises one or more members selected from the group consisting of antibiotics, analgesics, anti-inflammatories, and steroids.

5. The method of claim 1 wherein said biologically active substance comprises stem cells.

6. The method of claim 1 wherein said method further includes adding a radiographic contrast media to the intervertebral disc nucleus.

7. The method of claim 1 wherein said method further includes adding a polysaccharide to the intervertebral disc nucleus.

8. The method of claim 7 wherein said polysaccharide is a, proteoglycan and/or a hyaluronic acid.

9. The method of claim 1 wherein said method further includes adding a cross-linking agent to the intervertebral disc nucleus, to promote crosslinking of collagen molecules.

10. The method of claim 1 wherein said biologically active substance is effective for treating one or more medical conditions selected from the group consisting of degenerative disc disease, spinal arthritis, spinal infection, spinal, tumor, and osteoporosis.

11. The method of claim 1 wherein said plurality of particles of natural, collagen-rich tissue has a mean particle size of between 0.25 mm and 1.0 mm.

12. The method of claim 1 wherein said plurality of particles of natural, collagen-rich tissue has a mean particle size of between 0.25 mm and 0.5 mm.

13. The method of claim 1 wherein said plurality of particles of natural, collagen-rich tissue has a. mean particle size of between 0.5 mm and 1.0 mm.

14. The method of claim 1 wherein said plurality of particles of natural, collagen-rich tissue are added to the disc nucleus in a dehydrated state.

15. The method of claim 1 wherein said plurality of particles of natural, collagen-rich tissue are added to the disc nucleus in a non-dehydrated state.

16. The method of claim 1 wherein said plurality of particles of natural, collagen-rich tissue are added to the disc nucleus as a gel.

17. The method of claim 1 wherein said plurality of particles of natural, collagen-rich tissue are added to the disc nucleus as a suspension.

18. The method of claim 1 wherein said natural, collagen-rich tissue is an allograft tissue.

19. The method of claim 1 wherein said, natural, collagen-rich tissue is an autograft tissue.

20. The method of claim 1 wherein said natural, collagen-rich tissue is a xenograft tissue.

21. The method of claim 1 wherein said plurality of particles of natural, collagen-rich tissue, and said biologically active substance are surgically added simultaneously.

22. The method of claim 1 wherein said plurality of particles of natural, collagen-rich tissue, and said biologically active substance, are surgically added sequentially.

23. The method of claim, 1 wherein said, plurality of particles of natural, collagen-rich tissue, and said biologically active substance, are surgically added by needle injection.

24. The method of claim 1 wherein said plurality of particles of natural, collagen-rich tissue, and said biologically active substance, are surgically added by catheter infusion.

25. The method of claim 1 wherein said plurality of particles of natural, collagen-rich tissue, and said biologically active substance, are surgically added by extrusion.

* * * * *